(12) United States Patent
Dunfee et al.

(10) Patent No.: US 11,406,327 B2
(45) Date of Patent: Aug. 9, 2022

(54) IMAGING CATHETER ASSEMBLY

(71) Applicant: Canon U.S.A. Inc., Melville, NY (US)

(72) Inventors: Albert Harold Dunfee, Byfield, MA (US); Seiji Takeuchi, Newton, MA (US); Badr Elmaanaoui, Belmont, MA (US); Mark Alan Hamm, Lynnfield, MA (US)

(73) Assignee: Canon U.S.A., Inc., Melville, NY (US)

( * ) Notice: Subject to any disclaimer, the term of this patent is extended or adjusted under 35 U.S.C. 154(b) by 365 days.

(21) Appl. No.: 15/955,574

(22) Filed: Apr. 17, 2018

(65) Prior Publication Data

US 2019/0313975 A1 Oct. 17, 2019

(51) Int. Cl.
*A61B 5/00* (2006.01)
*A61M 25/01* (2006.01)
*A61M 25/00* (2006.01)

(52) U.S. Cl.
CPC .......... *A61B 5/6852* (2013.01); *A61B 5/0066* (2013.01); *A61M 25/0068* (2013.01); *A61M 25/0105* (2013.01); *A61B 5/0084* (2013.01); *A61M 2025/0004* (2013.01); *A61M 2025/0166* (2013.01)

(58) Field of Classification Search
CPC ... A61B 5/6852; A61B 5/0066; A61B 5/0084; A61M 25/0105; A61M 25/0068; A61M 2025/0004; A61M 2025/0166; A61M 25/007; A61M 2025/0681; A61M 25/0662
See application file for complete search history.

(56) References Cited

U.S. PATENT DOCUMENTS

| | | | |
|---|---|---|---|
| 4,878,893 | A | 11/1989 | Chin |
| 6,146,373 | A | 11/2000 | Cragg et al. |
| 6,558,355 | B1 | 5/2003 | Metzger et al. |
| 6,763,261 | B2 | 7/2004 | Casscells, III et al. |
| 6,860,876 | B2 | 3/2005 | Chen |
| 7,241,286 | B2 | 7/2007 | Atlas |
| 7,331,942 | B2 | 2/2008 | Alheidt et al. |
| 7,366,376 | B2 | 4/2008 | Shishkov et al. |
| 7,534,233 | B2 | 5/2009 | Schiller et al. |
| 7,625,366 | B2 | 12/2009 | Atlas |
| 7,717,899 | B2 | 5/2010 | Bowe |
| 7,842,026 | B2 | 11/2010 | Cahill et al. |

(Continued)

FOREIGN PATENT DOCUMENTS

| | | |
|---|---|---|
| EP | 2750599 A2 | 7/2014 |
| EP | 2928379 A1 | 10/2015 |
| WO | 2016/077252 A1 | 5/2016 |

*Primary Examiner* — Joseph M Santos Rodriguez
*Assistant Examiner* — Kaitlyn E Sebastian
(74) *Attorney, Agent, or Firm* — Canon U.S.A., Inc. IP Division

(57) ABSTRACT

An imaging catheter assembly comprising a catheter comprising: a proximal end; a distal end; a tubular body extending from the proximal end to the distal end; and an imaging element within the tubular body; a sheath comprising: a proximal end; a distal end; and a tubular body extending from the proximal end to the distal end, the tubular body having an inner surface, wherein the inner surface of the tubular body of the sheath at least partially defines a conduit for conveying a fluid to the distal end of the sheath, and wherein the sheath is movable such that the distal end of the sheath is positionable relative to the distal end of the catheter.

21 Claims, 10 Drawing Sheets

(56) References Cited

U.S. PATENT DOCUMENTS

| | | |
|---|---|---|
| 7,843,572 B2 | 11/2010 | Tearney et al. |
| 8,048,032 B2 | 11/2011 | Root et al. |
| 8,928,889 B2 | 1/2015 | Tearney et al. |
| 9,087,368 B2 | 7/2015 | Tearney et al. |
| 9,302,049 B2 | 4/2016 | Tekeste |
| 9,332,942 B2 | 5/2016 | Jaffer et al. |
| 9,557,154 B2 | 1/2017 | Tearney et al. |
| 2004/0267110 A1 | 12/2004 | Tremble |
| 2005/0085769 A1* | 4/2005 | MacMahon ......... A61M 25/007 604/96.01 |
| 2007/0073271 A1* | 3/2007 | Brucker ............ A61M 25/0043 604/537 |
| 2008/0058758 A1* | 3/2008 | Ranchod ............ A61M 25/007 604/508 |
| 2010/0076320 A1* | 3/2010 | Petersen ........... A61M 25/0069 600/478 |
| 2010/0092389 A1 | 4/2010 | Jaffer |
| 2011/0292400 A1 | 12/2011 | Fleming et al. |
| 2012/0253197 A1 | 10/2012 | Sadaka |
| 2013/0018448 A1 | 1/2013 | Folan et al. |
| 2013/0253474 A1* | 9/2013 | Farhangnia ....... A61M 25/0074 604/510 |
| 2014/0142427 A1 | 5/2014 | Petroff |
| 2014/0163383 A1* | 6/2014 | Van Hoven .............. A61B 8/12 600/467 |
| 2014/0180083 A1 | 6/2014 | Hoseit |
| 2014/0236103 A1 | 8/2014 | Fischell et al. |
| 2014/0276011 A1 | 9/2014 | Schmitt et al. |
| 2014/0276016 A1 | 9/2014 | Stigall et al. |
| 2016/0067444 A1* | 3/2016 | Allen .................. A61M 25/007 604/246 |
| 2017/0135584 A1 | 5/2017 | Tearney et al. |
| 2017/0209049 A1 | 7/2017 | Wang et al. |

* cited by examiner

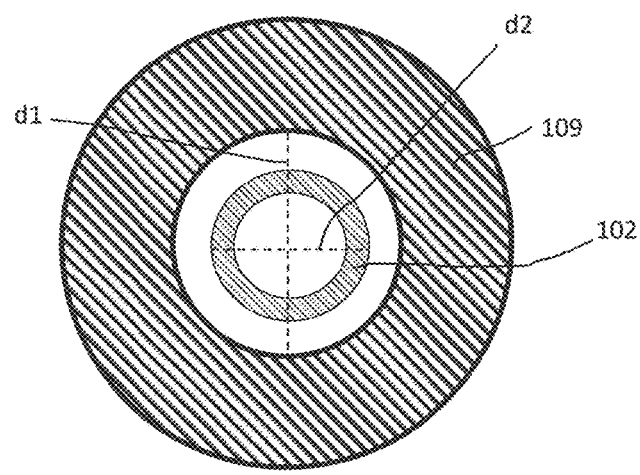
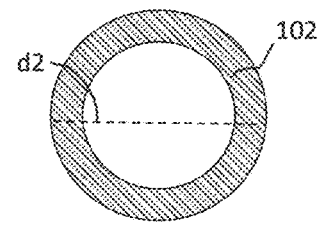
FIG.5　　　　　　　　　　　　FIG.6
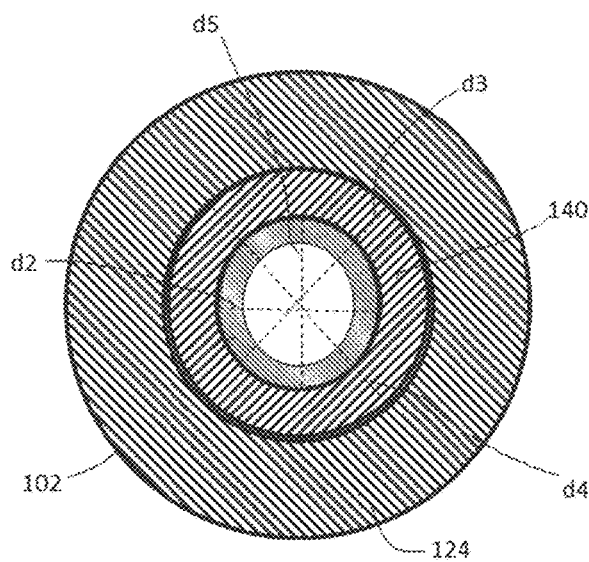
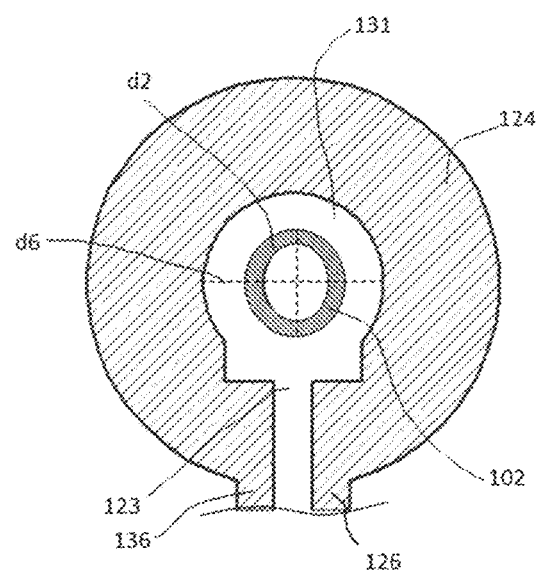
FIG.7　　　　　　　　　　　　FIG.8

IMAGING CATHETER ASSEMBLY

FIELD OF THE DISCLOSURE

The disclosure of this application relates generally to medical devices, and in particular it relates to an image catheter assembly for delivering flush solution.

BACKGROUND OF THE INVENTION

In order to obtain clear in-vivo images of arterial walls when using, for example, Optical Coherence Tomography (OCT), it is necessary to displace blood from a cylindrical volume around a tip of an imaging probe. To allow surveying of a length of an artery wall, it is desirable that the cylindrical volume be, for example, as long as approximately 40-50 mm or more. The better the blood is cleared from this volume, the better the image obtained of the arterial wall.

For example, in almost all uses of OCT for imaging during cardiac catheterizations, an imaging probe disposed within a guide catheter is inserted into an artery such that a direction of blood flow is from a proximal end of the imaging probe toward a distal end of the catheter or probe. It is desirable that a location of the cleared cylindrical volume be somewhat proximal to the distal end of the catheter. The guide wire is used to guide the imaging probe into the desired artery.

Previous and current methods of achieving the desired cleared volume or blood displacement have included the use of cardiac dilation balloons, the injection of contrast solution and/or saline through a guide catheter, and the injection of contrast solution and/or saline through a selective flush catheter inserted over the imaging catheter. Previous and current methods provide less than ideal solutions.

The balloon method either involves total occlusion of a vessel for the time that the image is desired, or the use of under-inflated balloons which does not completely remove the blood from the field of view. The guide flush method requires a large flow rate of contrast solution and/or saline that can over hydrate the patient. This method is also very ineffective when side branches are present. In particular, because the guide catheter sits loosely at the ostium, a high percentage of the flush solution does not actually make its way into the coronary artery, but gets carried away down the aorta into the rest of the body. It is well understood, many patients cannot process a high contrast burden during angioplasty which can lead to contrast-induced nephropathy (CIN).

U.S. Pat. No. 7,241,286 describes a flush catheter having an imaging catheter and a sheath affixed to an outer surface of the imaging catheter. The flush solution travels within the imaging catheter from a source until it exits the imaging catheter through a plurality of holes formed in the walls of the imaging catheter. The holes of the imaging catheter are positioned underneath the affixed sheath, thus the flow of the flush solution is directed by the affixed sheath along the outer surface of the imaging catheter in a proximal direction. However, because the sheath is affixed to the imaging catheter and must be located over the holes, the sheath is not moveable and there is no way for the operator to choose the location of the discharge of the flush solution relative to the distal end of the imaging catheter.

Thus, there is need for an imaging catheter assembly that avoids the above-noted problems and more efficiently delivers flush solution to the vessel, thereby allowing less flush media to be used and reducing the burden on the patient.

SUMMARY OF EXEMPLARY EMBODIMENTS

An imaging catheter assembly according to some example embodiments comprises a catheter comprising: a proximal end; a distal end; a tubular body extending from the proximal end to the distal end; and an imaging element within the tubular body; a sheath comprising: a proximal end; a distal end; and a tubular body extending from the proximal end to the distal end, the tubular body having an inner surface, wherein the inner surface of the tubular body of the sheath at least partially defines a conduit for conveying a fluid to the distal end of the sheath, and wherein the sheath is movable such that the distal end of the sheath is positionable relative to the distal end of the catheter An imaging catheter assembly according to some example embodiments comprises a catheter comprising: a proximal end; a distal end; a tubular body extending from the proximal end to the distal end, the tubular body having an outer surface; and an imaging element within the tubular body; a sheath comprising: a proximal end; a distal end; and a tubular body extending from the proximal end to the distal end, the tubular body having an inner surface, wherein the tubular body of the sheath coaxially surrounds the tubular body of the catheter to form an annular conduit defined by the outer surface of the tubular body of the catheter and the inner surface of the tubular body of the sheath, the annular conduit providing a pathway for conveying fluid to the distal end of the sheath, and wherein the sheath is movable along the outer surface of the tubular body of the catheter such that the distal end of the sheath is positionable relative to the distal end of the catheter A method of flushing an area within a coronary artery according to some example embodiments comprises providing an imaging catheter assembly comprising a catheter comprising: a proximal end; a distal end; a tubular body extending from the proximal end to the distal end; and an imaging element within the tubular body; a sheath comprising: a proximal end; a distal end; and a tubular body extending from the proximal end to the distal end, the tubular body having an inner surface, wherein the inner surface of the tubular body of the sheath at least partially defines a conduit; inserting the distal end of the catheter into the coronary artery to a predetermined position relative to the area within the coronary artery; positioning the distal end of the sheath to a predetermined position relative to the distal end of the catheter by advancing or retracting the sheath; and conveying a fluid to the distal end of the sheath via the conduit to flush the area within the coronary artery.

Further features will become apparent from the following description of exemplary embodiments with reference to the attached drawings.

BRIEF DESCRIPTION OF THE DRAWINGS

FIG. 5 is a cross-section view of the example imaging catheter assembly of FIG. 1 having the sheath in the first position, as viewed along line 5-5 of FIG. 2.

FIG. 6 is a cross-section view of the example imaging catheter assembly of FIG. 1 having the sheath in the first position, as viewed along line 6-6 of FIG. 2.

FIG. 7 is a cross-section view of the example imaging catheter assembly of FIG. 1 having the sheath in the first position, as viewed along line 7-7 of FIG. 2.

FIG. 8 is a cross-section view of the example imaging catheter assembly of FIG. 1 having the sheath in the first position, as viewed along line 8-8 of FIG. 2.

DESCRIPTION OF THE EMBODIMENTS

Figure 1:
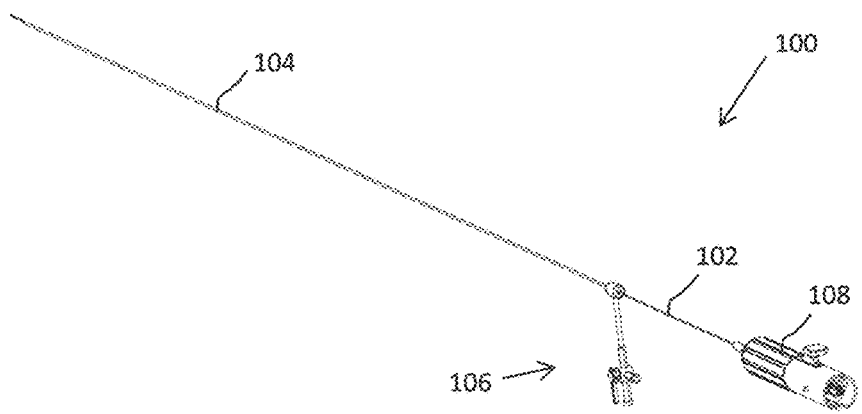
FIG. 1 is a perspective view of an example embodiment of an imaging catheter assembly.

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

Figure 2:
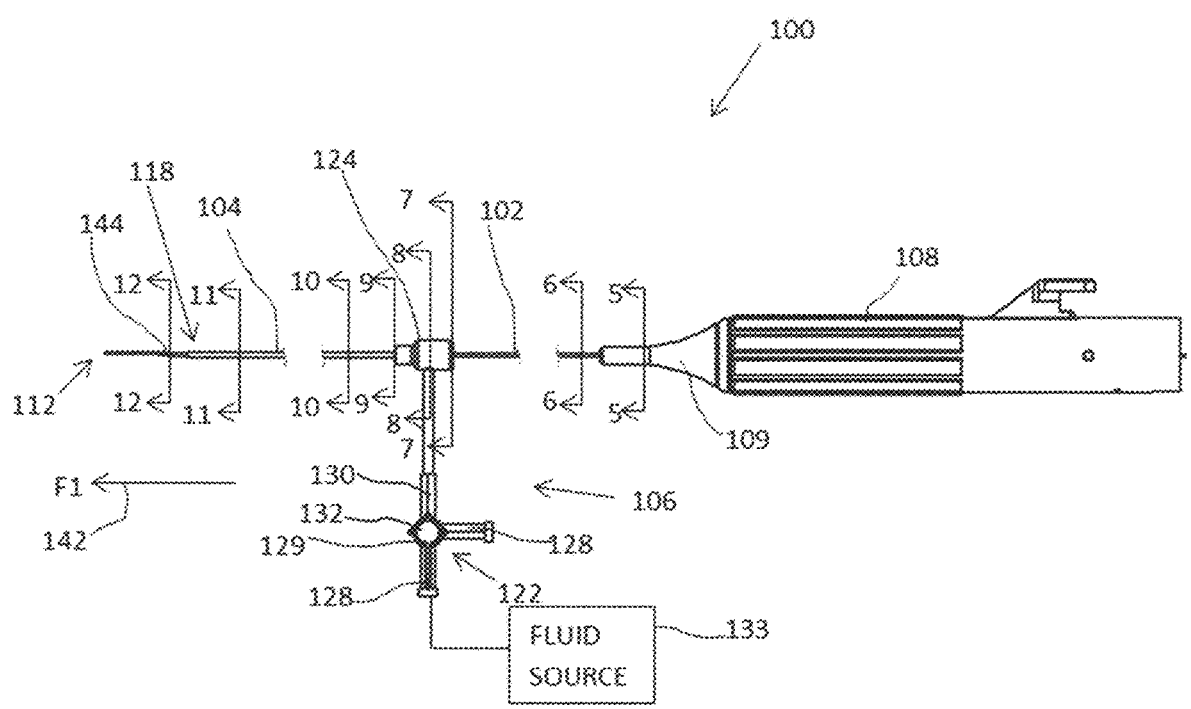
FIG. 2 is a side view of the example imaging catheter assembly of FIG. 1 having a sheath in a first position.
Figure 3:
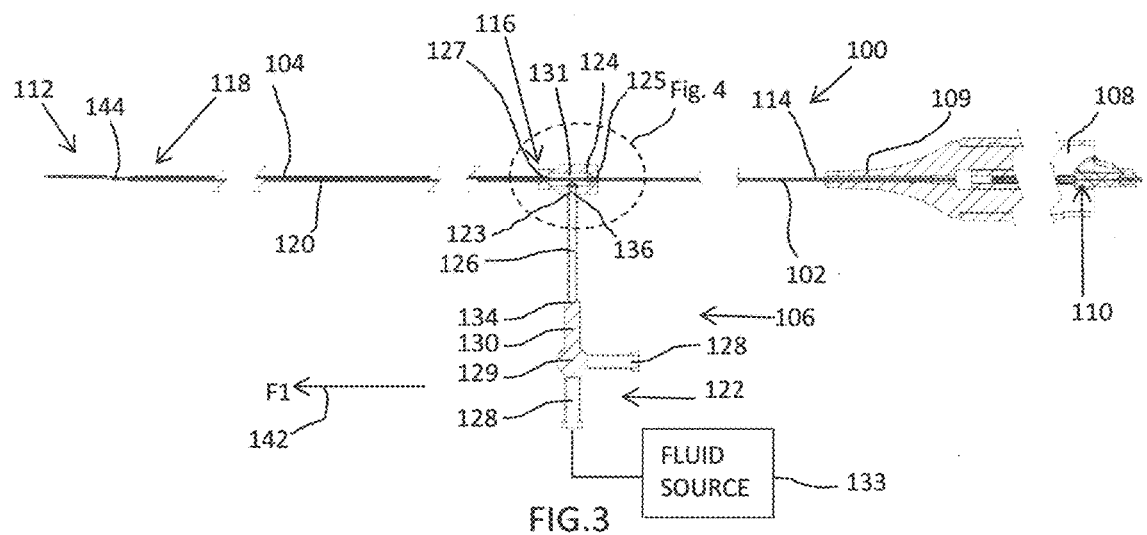
FIG. 3 is a cross-section view of the example imaging catheter assembly of FIG. 1 having the sheath in the first position, as viewed from a vertical plane cutting through the center of the imaging catheter assembly.

FIG. 1 is a perspective view of an example embodiment of an imaging catheter assembly 100. FIG. 2 is a side view of the imaging catheter assembly 100 in a first configuration. FIG. 3 is a cross-section view of the imaging catheter assembly 100, as viewed from a vertical plane cutting through the center of the imaging catheter assembly, in the first configuration. As shown in FIGS. 1-3, the imaging catheter assembly 100 may generally include a catheter 102, a sheath 104, a flow control mechanism 106, and a handle 108. The catheter 102 may be coupled with the handle 108. In the orientation shown in FIGS. 1-3, the catheter 102 is coupled with the handle 108.

The catheter may be made of a material that is transparent to the wavelengths of light used. For use with humans or animals, it is preferably that the catheter be made of a material that is biocompatible. The sheath is preferably transparent to allow light or other electromagnetic radiation to pass therethrough. Examples of suitable materials for either the catheter or the sheath include polyurethane, nylon, polyester, polyethylene, polyamide, polyimide, vinyl, silicone, and combinations thereof. An example suitable polyamide is TROGAMID, manufactured by Evonik Industries. An example suitable polyester is polyethylene terephthalate (PET). Another suitable material is polyether block amide (PEBA).

The catheter 102 and the sheath 104 may each have a tubular shape. As best seen in FIG. 3, the catheter 102 may have proximal end 110, a distal end 112, and a tubular body 114 extending from the proximal end 110 to the distal end 112. Similarly, the sheath 104 may have a proximal end 116, a distal end 118, and a tubular body 120 extending from the proximal end 116 to the distal end 118. As best seen in FIG. 3, the catheter 102 may extend into the handle 108 such that the proximal end 110 terminates within the handle 108. The strain relief 109 may be tapered such that it gradually decreases in diameter in a direction distally away from the distal end of the handle 108. In one aspect the strain relief 109 may be integral with the handle 108, while in another aspect, the strain relief 109 but be a separate piece connectable with the handle 108.

As best seen in FIGS. 1-3, the flow control mechanism 106 may include a multi-port valve 122, a housing member 124, and a connecting tube 126. The multi-port valve 122 may be any suitable valve that includes at least one inlet port 128 for receiving fluid from a fluid source 133, at least one outlet port 130 for outputting fluid, and a chamber 129 where the ports meet. In the example embodiment shown in FIGS. 1-3, the multi-port valve is a 3-way valve including three ports. The multi-port valve 122 may include an actuator 132 attached to a flow control mechanism (not shown) located within the chamber 129. Rotating the actuator 132 rotates the flow control mechanism within the chamber 129, thereby closing off or opening up communication between the ports 128, 130 and the chamber 129. Any suitable mechanism known in the art may be used to achieve this function, such as a ball valve. As is well understood in the art, the position of the actuator 132 may place any single port or any combination in ports in or out of communication with each other. Thus, when the actuator 132 is in an "off" position, the flow control mechanism is positioned to block fluid communication between the inlet ports 128 and the outlet port 130, while when the actuator 132 is in an "on" position, the flow control mechanism is in a position to allow for fluid communication between one or more of the inlet ports 128 and the outlet port 130.

Figure 4:
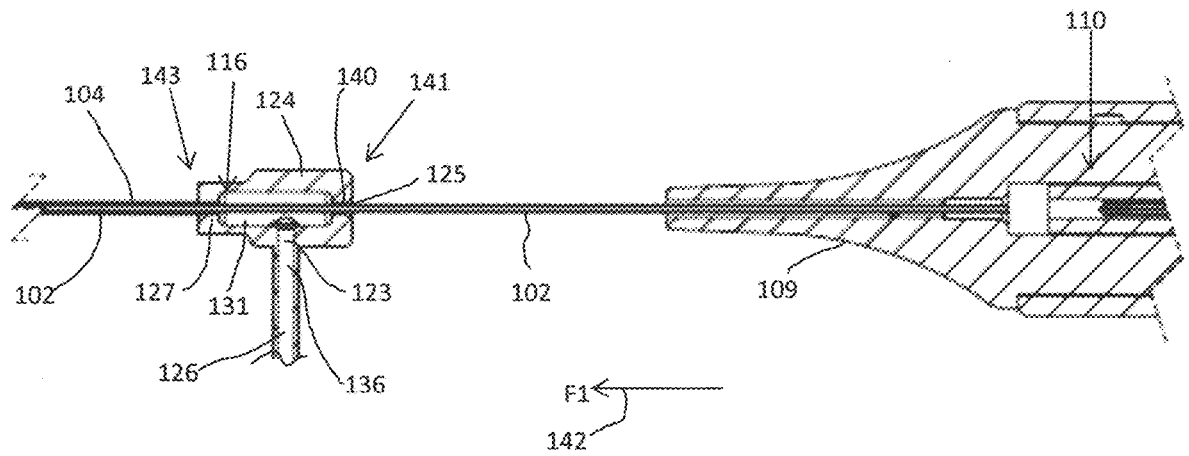
FIG. 4 is a close-up side view of a portion the example imaging catheter assembly of FIG. 1 having the sheath in the first position.

As seen in FIGS. 3 and 4, the housing member 124 may include a first port 123, a second port 125, a third port 127, and a chamber 131. In the orientation shown in FIG. 4, the third port 127 is at the distal end 143 of the housing member 124, the second port 125 is at the proximal end 141 of the housing member 124, and the first port 123 is midway between the proximal 141 and distal 143 ends of the housing member 124. The tube 126 has a first end 134 connected to one of the ports (e.g., the outlet port 130) of the multi-port valve 122 and a second end 136 connect to one of the ports (e.g., the first port 123) of the housing member 124. Thus, the tube 126 connects the multi-port valve 122 to the housing member 124. As best seen in FIG. 3, the tube 126 thereby provides flow path from a fluid source 133 connected to one of the inlet ports 128 to the chamber 131 of the housing member 124 via the first port 123. That is, when the actuator 132 is positioned such that a least one of the inlet ports 128 that is connected with a fluid source 133 is communication with the chamber 129 of the multi-port valve 122, and such that the outlet port 130 is also in communication with the chamber 131 of the housing member 124, the fluid may flow from the fluid source 133, through the inlet port 128, into the chamber 129 of the multi-port valve 122, out the outlet port 130, into the tube 126, through the first port 123 of the housing member 124, and into the chamber 131 of the housing member 124. In this manner, an operator may control the flow of from the fluid source 133 into the housing member 124 by employing the actuator 132.

As best seen in FIGS. 3 and 4, the housing member 124 may concentrically surround the sheath 104 at the distal end 143 and the entirety of the housing member 124 may concentrically surround the catheter 102. As further seen in FIGS. 3 and 4, the sheath 104 may concentrically surround the catheter 102 from the proximal end 143 of the housing 124 toward the distal end 112 of the catheter 102. That is, from outermost concentric structure to innermost concentric structure, the order of concentricity at the distal end 143 of the housing 124 may be housing member 124/sheath 104/catheter 102, while the area between the proximal end 141 of the housing 124 and the distal end 143 of the housing 124 may have an outermost to innermost centric order of housing member 124/catheter 102. As best seen in FIG. 4, the outer surface of the proximal end 116 of the sheath 104 may be fixed to the inner surface of the distal end 143 of the housing member 124 (e.g., at the port 127).

The housing 124 may include a seal member 140 at the proximal end 141 to prevent fluid from flowing out the proximal end 141 of the housing 124. The seal member 140 may be located concentrically around the catheter 102 and concentrically within the second port 125. The seal member 140 may generally be a circular flexible material that is biased toward compressing inwardly, such as an o-ring. The seal member 140 may be fixed to the inside surface of the second port 125 such as with an adhesive or the like. Because the seal member 140 is fixed to the inside surface of the housing member 124 in the second port 125 and is flexible, while the proximal end 116 of the sheath 104 is fixed to the inside surface of the housing member 124 in the third port 127, the sheath 104 and the housing member 124 are axially moveable as a unit relative to the handle 108 and the catheter 102. Moreover, because the housing member 124 is further connected to the tube 126 via the first inlet 123, and because the tube 126 is connected to the multi-port valve 122 via the outlet port 130, the entirety of the flow control mechanism 106, along with the sheath 104, is axially moveable as a unit relative to the handle 108 and the catheter 102. The catheter 102, and more particularly the distal end 112 having an imaging element 144, may be positioned within an artery at a predetermined position as part of a procedure for taking an image of the artery at the predetermined position. Once the catheter 102/imaging element 144 is positioned, the catheter is generally not moved as part of the process of taking the image. However, the sheath 104, while concentrically surrounding the catheter 102 is not attached to the catheter 102 in any manner. Thus, when a force F1 is applied in a direction 142 onto the flow control mechanism 106, the sheath 104 being attached to the housing member 124 can be advanced along the length of the catheter 102. Similarly, when a force F2 is applied in a direction 145 (FIG. 14), the sheath 104 can be retraced along the length of the catheter 102.

FIGS. 2-12 are various views of the imaging catheter assembly 100 in which the sheath 104 has been moved along direction 142 to a first position, i.e. the first configuration. FIGS. 13-22 are various views of the imaging catheter assembly 100 in which the sheath 104 has been moved along direction 145 to a second position, i.e., a second configuration. The first position of the sheath 104 is an extended/advanced position where the distal end 118 of the sheath 104 is located farther away from the proximal end 110 of the catheter 102, while the second position of the sheath 104 is a relatively retracted position where the distal end 118 of the sheath 104 is located closer to the proximal end 110 of the catheter 102. Put another way, in the first position the distal end 118 of the sheath 104 is located closer to the distal end 112 of the catheter 102, while in second position the distal end 118 of the sheath 104 is located farther from the distal end 112 of the catheter 102. While only two positions are shown, it should be understood that the sheath 104 can be positioned along the directions 142, 145 at any point along the catheter 102.

Starting with the first position, illustrated in FIGS. 2-12, as seen in FIGS. 2 and 3, the distal end 118 of the sheath 104 is located adjacent the distal end 112 of the catheter 102. More particularly, the distal end 118 of the sheath 104 is located adjacent the imaging element 144 that is located at the distal end 112 of the catheter 102. As also seen in FIGS. 2 and 3, the flow control mechanism 106 is positioned at a distance from the handle 108, such that the catheter 102 is visibly extending out the proximal end 141 of the of housing member 124. This is because the catheter 102 has a stationary position and the sheath 104 has been moved distally in the axial direction 142 by moving the entire flow control mechanism 106. As noted above, because the sheath 104 is fixed to the housing member 124, the application of force F1 in the direction 142 on the flow control mechanism 106 moves the sheath 104 distally in the direction 142.

The imaging element 144 may be any known device capable of imaging a portion of an artery, vessel, or other bodily cavity or orifice. For example, the imaging element 144 may include an outer casing in which an imaging probe (e.g., a wire or optical fiber), is disposed. The imaging probe may be designed to output a beam of light radially. The beam of light extends down a length of the imaging probe and is deflected radially by a mirror. The imaging probe may be rotated to provide a disk-like scan of a target, such as an inner wall of an artery, vessel, or other bodily cavity or orifice. The imaging probe may also be pulled lengthwise to scan a length of the target. The imaging element 144 including the imaging probe is preferably formed of a transparent material to allow the light beam to pass therethrough. For example, the casing may be formed of polyether block amide, known as PEBA, nylon and the imaging probe may be formed of, for example, silica glass. However, other materials may also be appropriate. Imaging systems that may be used with the probes and methods as described herein include, but are not limited to, the OCT imaging systems disclosed in U.S. Pat. Nos. 7,872,759; 8,289,522; 8,676,013; 8,928,889; 9,557,154 and U.S. Pat. Pub. 2017/0135584; and WO 2016/015052 to Tearney et al, as well as the disclosures directed to OCT and/or multimodality imaging disclosed in U.S. Pat. No. 9,332,942, and U.S. Patent Publication Nos. 2010/0092389; 2011/0292400; 2012/0101374; 2016/0228097; 2018/0003481; 2017/0360398; 2018/0045501; and WO 2016/144878 each of which patents and patent publications are incorporated by reference herein in their entireties.

FIGS. 5-12 illustrate various cross sections taken along lines 5-5 through 12-12 of FIG. 2. FIG. 5, which illustrates the cross section taken along line 5-5 of FIG. 2, shows the concentric configuration of elements located at line 5-5 when the sheath 104 is in the first position. As seen in FIG. 5, the outermost element is the strain relief 109, which concentrically surrounds the catheter 102. While not shown to scale in FIG. 5, in order to concentrically surround the catheter 102, the inner diameter d1 of the strain relief 109 is larger than the outer diameter d2 of the catheter 102. In one example aspect, the inner diameter d1 may be 25% larger than the outer diameter d2 to twice as large (i.e., d1=1.25 d2 to 2.0 d2), 35% larger to 90% larger (i.e., d1=1.35 d2 to 1.90 d2), or 50% larger to 75% larger (i.e., d1=1.5 d2 to 1.75 d2). In one example aspect the outer diameter d2 of the catheter 102 may be 0.400 mm to 1.000 mm, 0.500 mm to 0.950 mm, or 0.600 mm to 0.900 mm. Specific examples include 0.660 mm and 0.890 mm. The relative sizes of concentric elements discussed herein are defined relative to the outer diameter d2 of the catheter 102. Thus, the example dimensions of the inner diameter d2 of the catheter 102 may be used as a reference point for determining example dimensions of the other concentric elements discussed herein.

The strain relief 109 may also be several times thicker than the catheter 102. The strain relief 109 may have a thickness represented by the difference between the inner diameter and the outer diameter of the strain relief 109. The catheter 102 may have a thickness represented by the difference between the inner diameter and the outer diameter of the catheter 102. The ratio of the thickness of the strain relief 109 to the thickness of the catheter 102 may be from 3:1 to 15:1, 5:1 to 12:1, or 8:1 to 10:1. An example ratio is 10:1.

FIG. 6, which illustrates the cross section taken along line 6-6, of FIG. 2, shows the configuration of elements located at line 6-6 when the sheath 104 is in the first position. As seen in FIG. 6, at the first position, the catheter 102 is the only element located at line 6-6. That is, when the sheath 104 has been advanced forward in the direction 142, only the catheter 102 is present in the area extending from the proximal end 141 of the housing member 124 to the distal end of the strain relief 109.

FIG. 7, which illustrates the cross section taken along line 7-7 of FIG. 2, shows the configuration of concentric elements located at line 7-7 when the sheath 104 is in the first position. As seen in FIG. 2, the line 7-7 is located at the proximal end 141 of the housing member 124. As seen in FIG. 7, at this location, the outermost element is the housing member 124 of the flow control mechanism 106, which concentrically surrounds the seal member 140, which in turn concentrically surrounds the catheter 102. That is, the order of concentric elements from outermost to innermost along line 7-7 is the housing member 124/seal member 140/catheter 102. Notably, the sheath 104 is not located at the proximal end 141 of the housing 124. However, the seal member 140 is present. As noted above, the seal member 140 serves as a fluid blocking member that prevents fluid in the chamber 131 from flowing out of the proximal end 141 of the housing 124. That is, once fluid fills the chamber 131, the fluid is directed distally toward the distal end 118 of the sheath 104 and prevented from flowing out the proximal end 141 of the housing member 124 by virtue of the seal member 140.

While not shown to scale in FIG. 7, in order to successfully seal the proximal end 141 of the housing member 124, the outer diameter d3 of the sealing member 140 is approximately equal to the inner diameter d4 of the proximal end 141 of the housing member 124, while the inner diameter d5 of the sealing member 140 is approximately equal to the outer diameter d2 of the catheter 102. However, as noted above, because the seal member 140 is flexible, it is possible to move the flow control mechanism along the length of the catheter 102 when sufficient force F1 is applied in the direction 142. In one example aspect, the outer diameter d3 (or inner diameter d4) may be twice as large as the inner diameter d5 (or outer diameter d2) to 6 times as large (i.e., d3 (or d4)=2.0 d5 (or d2) to 6.0 d5 (or d2)), or 3 times as large to 5 times as large (i.e., d3 (or d4)=3.0 d5 (or d2) to 5.0 d5 (or d2)). Examples includes the outer diameter d3 being 2 times or 3 times larger than the inner diameter d5.

FIG. 8, which illustrates the cross section taken along line 8-8 of FIG. 2, shows the configuration of concentric elements located at line 8-8 when the sheath 104 is in the first position. As seen in FIG. 2, the line 8-8 is located midway between the proximal end 141 and distal end 143 of the housing member 124. As seen in FIG. 8, at this location, the outermost element is the housing member 124 of the flow control mechanism 106, which concentrically surrounds the catheter 102. However, as also shown in FIG. 8, there is a space between the outside surface of the catheter 102 and the inside surface of the housing member 124, defining the chamber 131. That is, the chamber 131 is defined by the area between the outer diameter d2 of the catheter 102 and an inner diameter d6 of the housing member 124. Notably, the inner diameter d6 of the housing member 124 in the area between the proximal 141 and distal 143 ends may be significantly larger than the inner diameter d4 of the housing member 124 at the proximal end 141 (or at the distal end 143 as discussed below with respect to FIG. 9). This difference in diameter allows for a volume of liquid to fill the chamber 131 when supplied from the fluid source 133 via the tube 126. While not shown to scale in FIG. 8, in one example aspect, the inner diameter d6 may be five times as large the outer diameter d2 to twenty times as large (i.e., d6=5.0 d2 to 20.0 d2), seven times as large to fifteen times as large (i.e., d6=7.0 d2 to 15.0 d2), or nine times as large to twelve times as large (i.e., d6=9.0 d2 to 12.0 d2). In one example aspect, the inner diameter d6 may be ten times as large as the outer diameter d2 (i.e., d6=10.0 d2).

Figure 9:
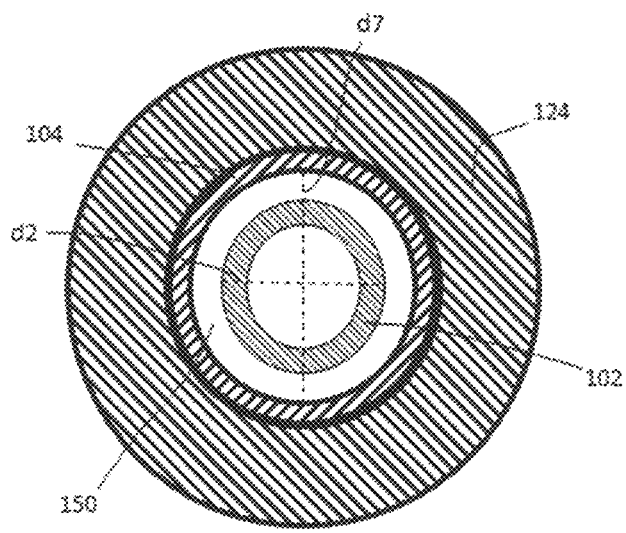
FIG. 9 is a cross-section view of the example imaging catheter assembly of FIG. 1 having the sheath in the first position, as viewed along line 9-9 of FIG. 2.

FIG. 9, which illustrates the cross section taken along line 9-9 of FIG. 2, shows the configuration of concentric elements located at line 9-9 when the sheath 104 is in the first position. As seen in FIG. 2, the line 9-9 is at the distal end 143 of the housing member 124. As seen in FIG. 8, at this location, the outermost element is the housing member 124 of the flow control mechanism 106, which concentrically surrounds the, sheath 104, which concentrically surrounds the catheter 102. That is, the order of concentric elements from outermost to innermost along line 9-9 is the housing member 124/the sheath 104/the catheter 102. However, as also shown in FIG. 9, there is a space between the outside surface of the catheter 102 and the inside surface of the sheath 104, defining a conduit 150. That is, the conduit 150 is defined by the area between the outer diameter d2 of the catheter 102 and an inner diameter d7 of sheath 104. Notably, the inner diameter d7 of the sheath 104 is significantly larger than the outer diameter d2 of the catheter 102. This difference in diameter defines the conduit 150 and allows for a volume of liquid to flow from the chamber 131 into the conduit 150. As best seen in FIG. 4, the proximal end 116 of the sheath 104 has an open end that is in communication with the chamber 131. When liquid travels into and fills the chamber 131, the liquid will then travel into the conduit 150 defined between the catheter 102 and the sheath 104 and continue to travel until reaching the distal end 118 of the sheath 104, which has another open end. In this manner, the conduit 150 is an annular space for delivering liquid. While not shown to scale in FIG. 9, in one example aspect, the inner diameter d7 may be 25% larger than the outer diameter d2 to four times as large (i.e., d7=1.25 d2 to 4.0 d2), 50% larger to three times larger (i.e., d7=1.50 d2 to 3.0 d2), or 75% larger to 2.5 times as large (i.e., d7=1.75 d2 to 2.5 d2). In one example, the inner diameter d7 may be 75% larger than the outer diameter d2 (i.e., d7=1.75 d2).

Figure 10:
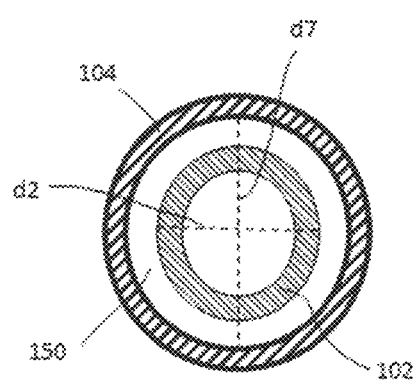
FIG. 10 is a cross-section view of the example imaging catheter assembly of FIG. 1 having the sheath in the first position, as viewed along line 10-10 of FIG. 2.

FIG. 10, which illustrates the cross section taken along line 10-10 of FIG. 2, shows the configuration of concentric elements located at line 10-10 when the sheath 104 is in the first position. As seen in FIG. 2, the line 10-10 is located distally relative to the housing member 124, but much closer to the housing member 124 than the distal end 112 of the catheter 102. As seen in FIG. 10, at this location, the outermost element is the sheath 104, which concentrically surrounds the catheter 102. That is, the order of concentric elements from outermost to innermost along line 10-10 is the sheath 104/the catheter 102. As also shown in FIG. 10, the conduit 150 is present between the sheath 104 and the catheter 102 at this location. That is, the conduit 150 continues to extend along the catheter 102 as long as the sheath 104 has not yet terminated.

Figure 11:
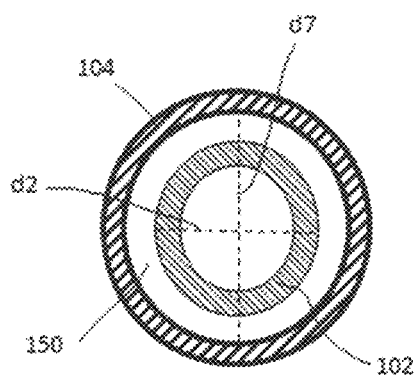
FIG. 11 is a cross-section view of the example imaging catheter assembly of FIG. 1 having the sheath in the first position, as viewed along line 11-11 of FIG. 2.

FIG. 11, which illustrates the cross section taken along line 11-11 of FIG. 2, shows the configuration of concentric elements located at line 11-11 when the sheath 104 is in the first position. As seen in FIG. 2, the line 11-11 is located distally relative to the housing member 124, but much closer to the distal end 112 of the catheter 102 than the housing member 124. As seen in FIG. 11, at this location, the outermost element is the sheath 104, which concentrically surrounds the catheter 102. That is, the order of concentric elements from outermost to innermost along line 11-11 is the sheath 104/the catheter 102. As also shown in FIG. 11, the conduit 150 is present between the sheath 104 and the catheter 102 at this location. That is, the conduit 150 continues to extend along the catheter 102 as long as the sheath 104 has not yet terminated. FIG. 11 is best compared to FIG. 21, discussed below. Even though the cross-section of FIG. 11 is taken at the same point along the length of the catheter 102 as the cross-section of FIG. 21, the cross-section of FIG. 21 does not include the sheath 104. This is because in the second position, the sheath 104 is retracted relative to the first position, and the distal end 118 of the sheath 104 terminates farther from the distal end 112 of the catheter 102 than in the first position.

Figure 12:
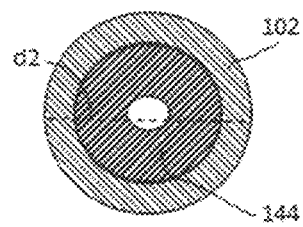
FIG. 12 is a cross-section view of the example imaging catheter assembly of FIG. 1 having the sheath in the first position, as viewed along line 12-12 of FIG. 2.

FIG. 12, which illustrates the cross section taken along line 12-12 of FIG. 2, shows the configuration of concentric elements located at line 12-12 when the sheath 104 is in the first position. As seen in FIG. 2, the line 12-12 is located at the distal end 112 of the catheter 102. As seen in FIG. 12, at the first position, the catheter 102 located at line 12-12, but the sheath 104 is not present. That is, the distal end 118 of the sheath 102 terminates just before the distal end 112 of the catheter 102, in the first position. As shown schematically in FIG. 12, the imaging element 144 may be located within the catheter 102 at the distal end 112 of the catheter 102. The distal end 118 of the sheath 104 is an opening of the tubular body 120 of the sheath 104. Thus, because the distal end 118 of the sheath 104 terminates just before the distal end 112 of the catheter 102, fluid traveling through the conduit 150 will exit the conduit 150 at the distal end 118 of the sheath 104 and flush the artery area near the distal end 112 of the catheter 102.

Figure 13:
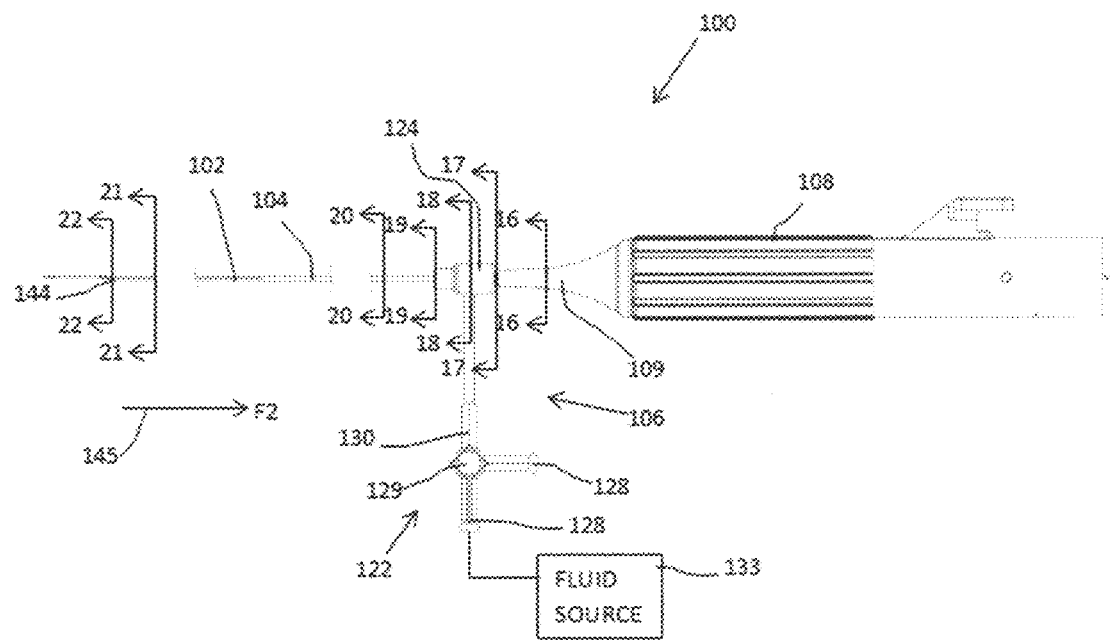
FIG. 13 a side view of the example imaging catheter assembly of FIG. 1 having the sheath in a second position.
Figure 14:
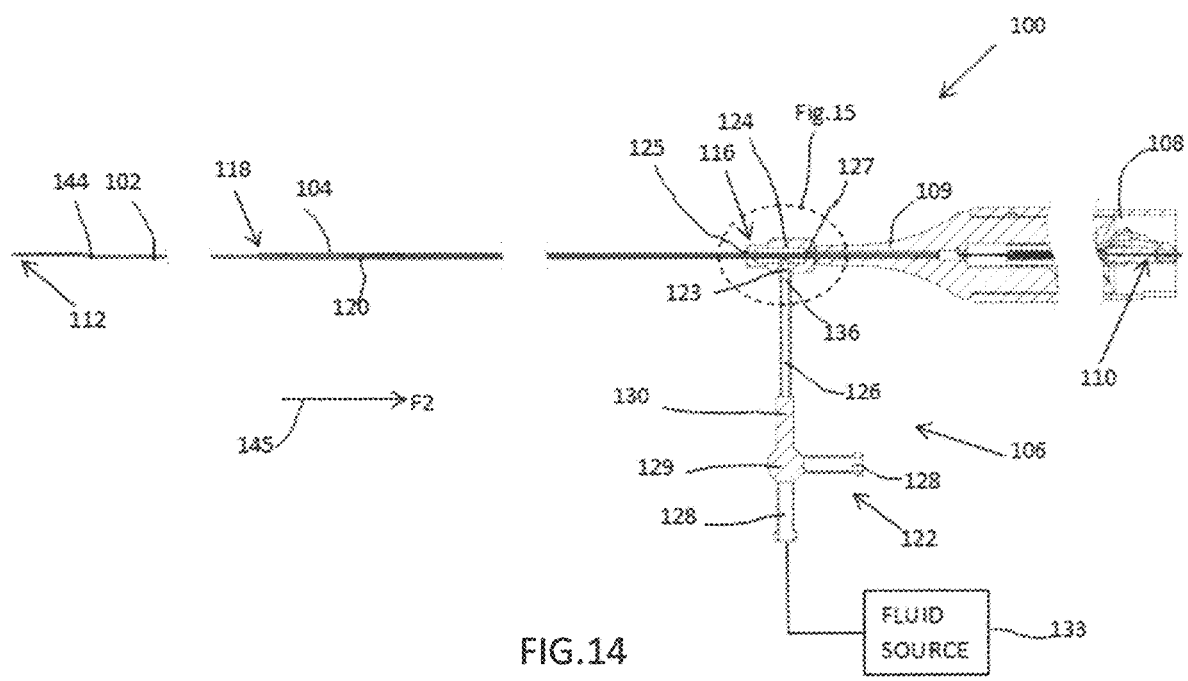
FIG. 14 is a cross-section view of the example imaging catheter assembly of FIG. 1 having the sheath in the second position, as viewed from a vertical plane cutting through the center of the imaging catheter assembly.
Figure 15:
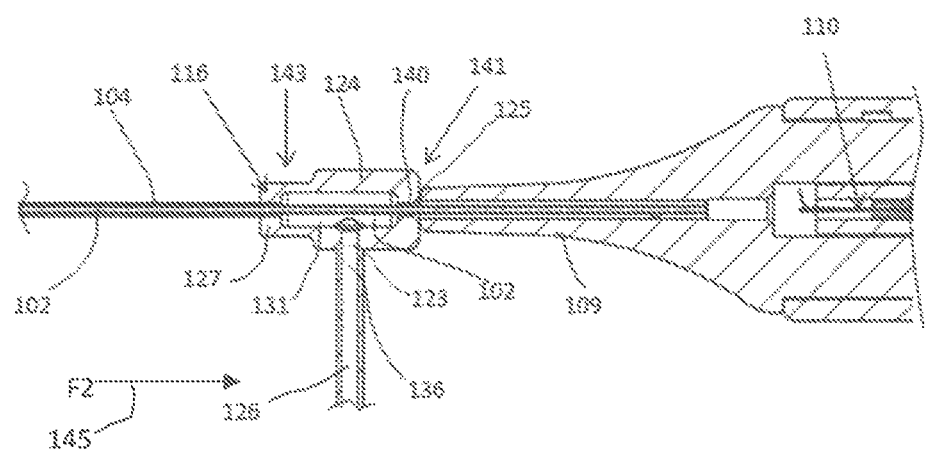
FIG. 15 is a close-up side view of a portion the example imaging catheter assembly of FIG. 1 having the sheath in the second position.

Turning to the second position, illustrated in FIGS. 13-22, as seen in FIGS. 13 and 14, the distal end 118 of the sheath 104 is located at a distance from the distal end 112 of the catheter 102 as compared to the first position. More particularly, the distal end 118 of the sheath 104 is located at distance from the imaging element 144 that is located at the distal end 112 of the catheter 102. As also seen in FIGS. 13 and 14, the flow control mechanism 106 is positioned flush against the handle 108, such that the catheter 102 is not visible extending out the proximal end 141 of the housing member 124. This is because the catheter 102 has a stationary position and the sheath 104 has been retraced proximally in the direction 145 by moving the entire flow control mechanism 106. As noted above, because the sheath 104 is fixed to the housing member 124, the application of force F2 in the direction 145 on the flow control mechanism 106 moves the sheath 104 proximally in the direction 145.

Figure 16:
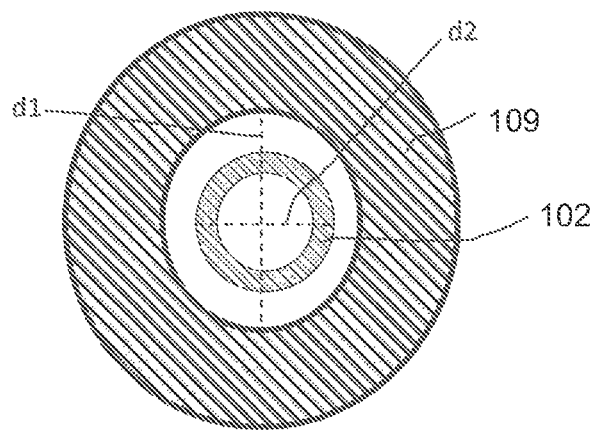
FIG. 16 is a cross-section view of the example imaging catheter assembly of FIG. 1 having the sheath in the second position, as viewed along line 16-16 of FIG. 13.

FIGS. 16-22 illustrate various cross sections taken along line 16-16 through line 22-22 of FIG. 13. FIG. 16, which illustrates the cross section taken along line 16-16, of FIG. 13, shows the concentric configuration of elements located at line 16-16 when the sheath 104 is in the second position. As seen in FIG. 16, the outermost element is the strain relief 109, which concentrically surrounds the catheter 102. Notably, line 16-16 of FIG. 13 is located in the corresponding location as line 5-5 of FIG. 2. However, because FIG. 2 illustrates the first configuration where the sheath 104 in first position, while FIG. 13 illustrates the second configuration where the sheath 104 is in the second position, the concentric elements are different. That is, in the corresponding location, in the first configuration only the catheter 102 is present, while in the second configuration the strain relief 109 concentrically surrounds the catheter 102.

Figure 17:
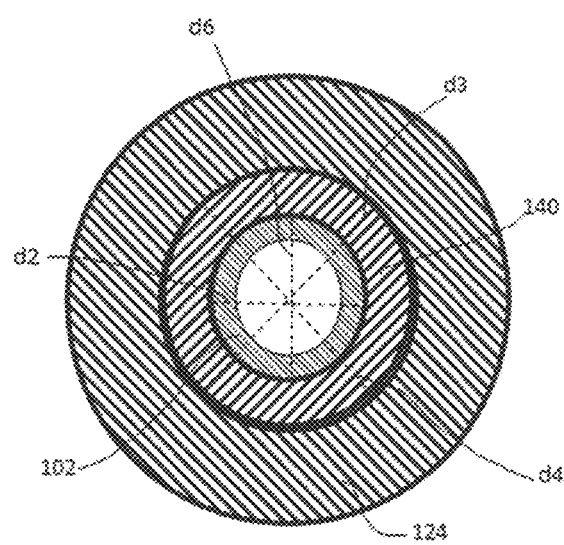
FIG. 17 is a cross-section view of the example imaging catheter assembly of FIG. 1 having the sheath in the second position, as viewed along line 17-17 of FIG. 13.

FIG. 17, which illustrates the cross section taken along line 17-17 of FIG. 13, shows the configuration of concentric elements located at line 17-17 when the sheath 104 is in the second position. As seen in FIG. 13, the line 17-17 is located at the proximal end 141 of the housing member 124. As seen in FIG. 17, at this location, the outermost element is the housing member 124 of the flow control mechanism 106, which concentrically surrounds the seal member 140, which in turn concentrically surrounds the catheter 102. That is, the order of concentric elements from outermost to innermost along line 17-17 is the housing member 124/seal member 140/catheter 102. Notably, the elements along line 17-17 of FIG. 13 are the same as the elements along line 7-7 of FIG. 2. Thus, at the proximal end 141 of the housing member 124, the structure is the same in both the first configuration and the second configuration.

Figure 18:
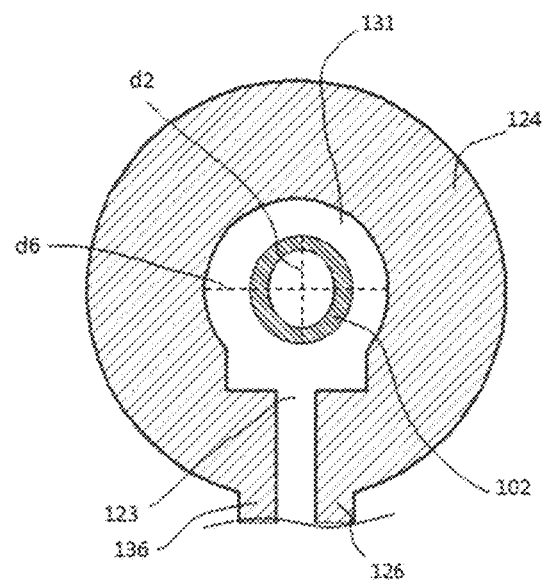
FIG. 18 is a cross-section view of the example imaging catheter assembly of FIG. 1 having the sheath in the second position, as viewed along line 18-18 of FIG. 13.

FIG. 18, which illustrates the cross section taken along line 18-18 of FIG. 13, shows the configuration of concentric elements located at line 18-18 when the sheath 104 is in the second position. As seen in FIG. 13, the line 18-18 is located midway between the proximal end 141 and distal end 143 of the housing member 124. As seen in FIG. 18, at this location, the outermost element is the housing member 124 of the flow control mechanism 106, which concentrically surrounds the catheter 102. However, as also shown in FIG. 18, there is a space between the outside surface of the catheter 102 and the inside surface of the housing member 124, defining the chamber 131. That is, the chamber 131 is defined by the area between the outer diameter d2 of the catheter 102 and an inner diameter d6 of the housing member 124. Notably, the elements along line 18-18 of FIG. 13 are the same as the elements along line 8-8 of FIG. 2. Thus, at the point midway between the proximal end 141 and the distal end 143 of the housing member 124, the structure is the same in both the first configuration and the second configuration.

Figure 19:
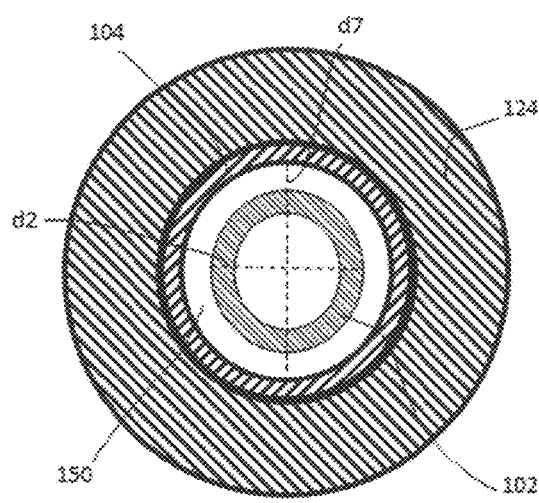
FIG. 19 is a cross-section view of the example imaging catheter assembly of FIG. 1 having the sheath in the second position, as viewed along line 19-19 of FIG. 13.

FIG. 19, which illustrates the cross section taken along line 19-19 of FIG. 13, shows the configuration of concentric elements located at line 19-19 when the sheath 104 is in the second position. As seen in FIG. 13, the line 19-19 is at the distal end 143 of the housing member 124. As seen in FIG. 19, at this location, the outermost element is the housing member 124 of the flow control mechanism 106, which concentrically surrounds the, sheath 104, which concentrically surrounds the catheter 102. That is, the order of concentric elements from outermost to innermost along line 19-19 is the housing member 124/the sheath 104/the catheter 102. However, as also shown in FIG. 19, there is a space between the outside surface of the catheter 102 and the inside surface of the sheath 104, defining the conduit 150. That is, the conduit 150 is defined by the area between the outer diameter d2 of the catheter 102 and an inner diameter d7 of sheath 104. Notably, the elements along line 19-19 of FIG. 13 are the same as the elements along line 9-9 of FIG. 2. Thus, at the distal end 143 of the housing member 124, the structure is the same in both the first configuration and the second configuration.

Figure 20:
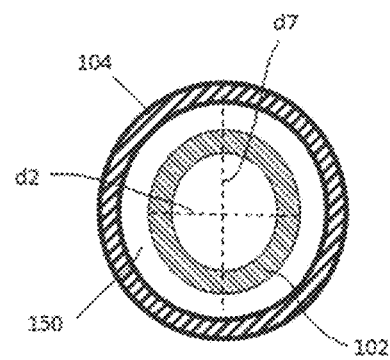
FIG. 20 is a cross-section view of the example imaging catheter assembly of FIG. 1 having the sheath in the second position, as viewed along line 20-20 of FIG. 13.

FIG. 20, which illustrates the cross section taken along line 20-20 of FIG. 13, shows the configuration of concentric elements located at line 20-20 when the sheath 104 is in the second position. As seen in FIG. 13, the line 20-20 is located distally relative to the housing member 124, but much closer to the housing member 124 than the distal end 112 of the catheter 102. As seen in FIG. 20, at this location, the outermost element is the sheath 104, which concentrically surrounds the catheter 102. That is, the order of concentric elements from outermost to innermost along line 20-20 is the sheath 104/the catheter 102. As also shown in FIG. 20, the conduit 150 is present between the sheath 104 and the catheter 102 at this location. That is, the conduit 150 continues to extend along the catheter 102 as long as the sheath 104 has not yet terminated. Notably, line 20-20 of FIG. 13 is located in the corresponding location as line 10-10 of FIG. 2. The elements along line 20-20 of FIG. 13 are the same as the elements along line 10-10 of FIG. 2.

Thus, at this location, the structure is the same in both the first configuration and the second configuration.

Figure 21:
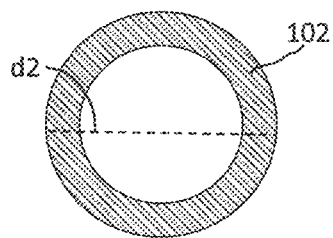
FIG. 21 is a cross-section view of the example imaging catheter assembly of FIG. 1 having the sheath in the second position, as viewed along line 21-21 of FIG. 13.

FIG. 21, which illustrates the cross section taken along line 21-21 of FIG. 13, shows the configuration of concentric elements located at line 21-21 when the sheath 104 is in the second position. As seen in FIG. 13, the line 21-21 is located distally relative to the housing member 124, but much closer to the distal end 112 of the catheter 102 than the housing member 124. As seen in FIG. 21, at this location, only the catheter 102 is present. That is, the sheath 104 has terminated at this location along with the conduit 150. Notably, line 21-21 of FIG. 13 is located in the corresponding location as line 11-11 of FIG. 2. The elements along line 21-21 of FIG. 13 are different from the elements along line 11-11 of FIG. 2 in that the sheath 104 is present in FIG. 11, but not present in FIG. 21. This is because in the second configuration, the sheath 104 is retracted relative to the first configuration, and the distal end 118 of the sheath 104 terminates farther from the distal end 112 of the catheter 102 in the second configuration than in the first configuration.

Figure 22:
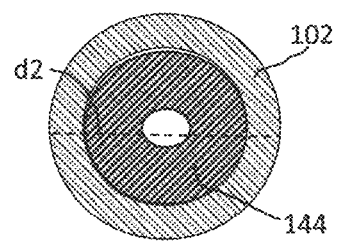
FIG. 22 is a cross-section view of the example imaging catheter assembly of FIG. 1 having the sheath in the second position, as viewed along line 22-22 of FIG. 13.

FIG. 22, which illustrates the cross section taken along line 22-22 of FIG. 13, shows the configuration of concentric elements located at line 22-22 when the sheath 104 is in the second position. As seen in FIG. 13, the line 22-22 is located at the distal end 112 of the catheter 102. As seen in FIG. 22, at the second position, the catheter 102 is located at line 22-22, but not the sheath 104 because the sheath 104 terminated farther away in the proximal direction. As shown schematically in FIG. 22, the imaging element 144 may be located within the catheter 102 at the distal end 112 of the catheter 102. Notably, line 22-22 of FIG. 13 is located in the corresponding location as line 12-12 of FIG. 2. The elements along line 22-22 of FIG. 13 are the same as the elements along line 12-12 of FIG. 2. Thus, at this location, the structure is the same in both the first configuration and the second configuration.

While two positions of the sheath 104 have been illustrated as examples, it should be understood that the sheath 104 can be positioned anywhere along the length of the catheter 102 as desired by the operator. That is, the operator can position the sheath 104 along the length of the catheter 102 by moving the housing member 124 together with the sheath 104 by applying the force F1 in the direction 142 or by applying the force F2 in the direction 145.

Figure 23:
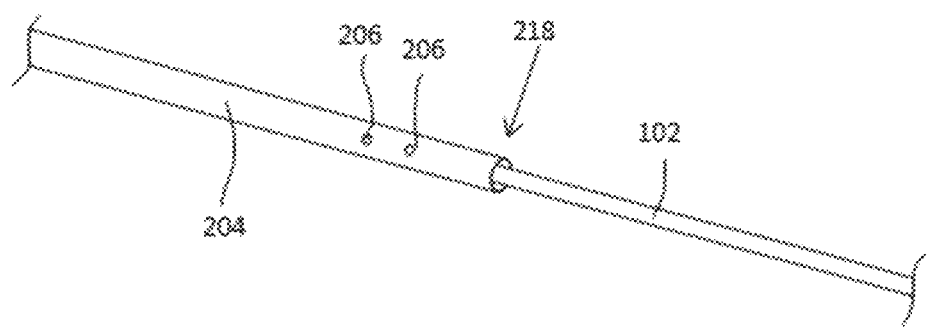
FIG. 23 is a perspective view of a portion an example embodiment of a sheath that may be used in conjunction with an embodiment of an imaging catheter assembly.

FIG. 23 is a perspective view of a portion an example embodiment of a sheath 204 that may be used in conjunction with an embodiment of an imaging catheter assembly 100. The sheath 204 is similar to the sheath 104 described above and similarly concentrically surrounding the catheter 102. That is, the sheath 204 may be used in place of the sheath 104 in the image catheter assembly 100. The only difference between the sheath 204 illustrated in FIG. 23 and the sheath 104 is that the sheath 204 includes a plurality of holes 206. The holes 206 provide another exit for the fluid traveling through the annular conduit formed between the outer surface of the catheter 102 and the inner surface of the sheath 204. In other words, while the fluid travels within the conduit between the outer surface of the catheter and the inner surface of the sheath 204 toward the distal end 218 of the sheath 204, some of the fluid will exit out of the holes 206, while some of the fluid will continue to exit out the distal end 218. While two holes 206 have been illustrated on one of the sheath 204, any number of holes may be located at any number of locations along the length and along the circumference of the sheath 204. Furthermore, the size of the holes may be varied. The number, position, and size of the holes 206 may be optimized based on the desired flow pattern.

Figure 24:
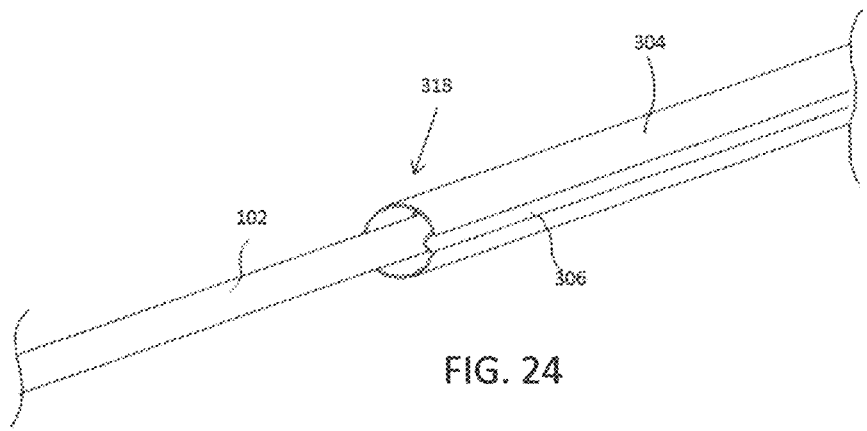
FIG. 24 is a perspective view of a portion another example embodiment of a sheath that may be used in conjunction with an embodiment of an imaging catheter assembly.

FIG. 24 is a perspective view of a portion another example embodiment of a sheath 304 that may be used in conjunction with an embodiment of an imaging catheter assembly. The sheath 304 is similar to the sheath 104 described above and similarly concentrically surrounding the catheter 102. That is, the sheath 304 may be used in place of the sheath 104 in the image catheter assembly 100. The only difference between the sheath 304 illustrated in FIG. 24 and the sheath 104 is that the sheath 304 includes a channel 306. The channel 306 may extend along the entire outer surface of the sheath 304 from the proximal end (not shown) to the distal end 318. The channel 306 may be sized to receive a guidewire that is used as part of image processing. The guidewire is discussed below in more detail in the context of imaging process. As seen in FIG. 24, the channel 306 may be shaped as a semi-circle concavity and may protrude toward the outer surface of the catheter 102. By protruding toward the outer surface of the catheter 102, the sheath 304 provides a space for the guidewire to fit, thereby providing for more annular space around the sheath 304. In another example embodiment, the channel may instead by formed on the inside surface of the sheath, such that the guidewire would pass through the conduit between the sheath and the catheter.

Figure 25A:
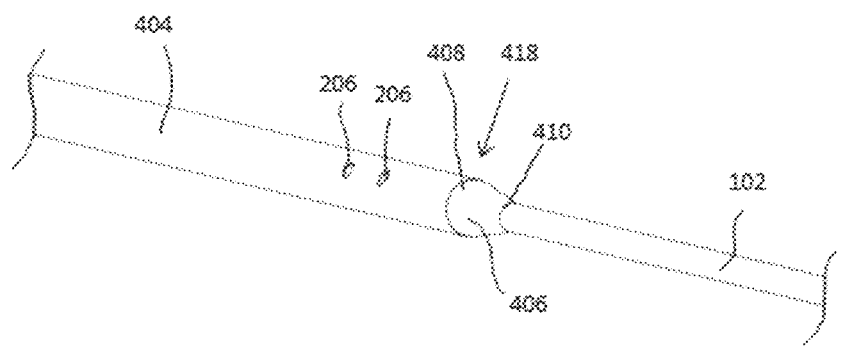
FIG. 25A is a perspective view of a portion of another example embodiment of a sheath in a first orientation, which may be used in conjunction with an embodiment of an imaging catheter assembly.
Figure 25B:
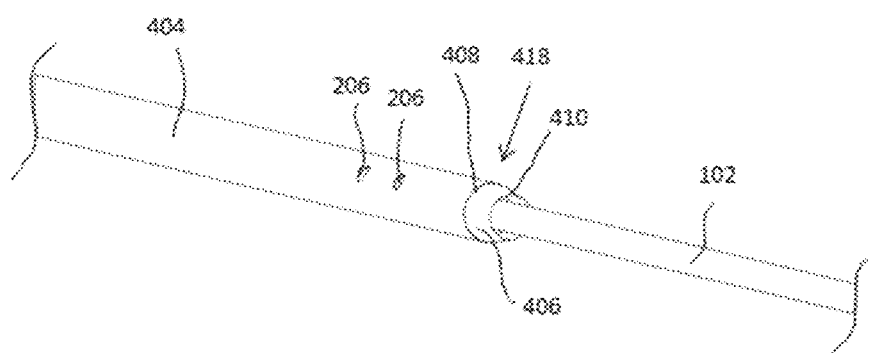
FIG. 25B is a perspective view of the example sheath of FIG. 25A, in a second orientation.

FIGS. 25A and 25B are perspective views of a portion of another example embodiment of a sheath 404 that may be used in conjunction with an embodiment of an imaging catheter assembly. FIG. 25A shows the sheath 404 in a first orientation and FIG. 25B shows the sheath 404 in a second orientation. The sheath 404 is similar to the sheath 104 described above and similarly concentrically surrounding the catheter 102. That is, the sheath 404 may be used in place of the sheath 104 in the image catheter assembly 100. The only difference between the sheath 404 illustrated in FIGS. 25A and 25B and the sheath 104 is that the sheath 404 includes a flexible tip 406. As seen in FIGS. 25A and 25B, the flexible tip 406 may extend from the distal end 418 of the sheath 404. The flexible tip 406 may have a conical shape where a first end 408 has a larger diameter than a second end 410. FIG. 25A illustrates a first orientation of the flexible tip 406, where the second end of 410 of the flexible tip 406 is in contact with the outer surface of the catheter 102, i.e., in an contracted orientation. FIG. 25B illustrates a second orientation of the flexible tip 406, where the second end 410 of the flexible tip 406 is not in contact with the catheter 102, i.e., in an expanded orientation. The flexible tip 406 may be made from a flexible material that has an internal force that biases the flexible tip 406 toward the contracted orientation shown in FIG. 25A. That is, when no force or insufficient force is applied to the flexible tip 406 in a direction radially outward from the catheter 102 against the flexible tip 406, the flexible tip 406 will bias to the contracted orientation and will be in contact with the outer surface of the catheter 102. However, when sufficient pressure to overcome the bias force is provided in a direction radially outward from the catheter 102 against the flexible tip 406, the flexible tip 406 will expand away from the surface of the catheter 102 to the expanded orientation shown in FIG. 25B. The application of pressure may be provided by the flow of fluid through the annular conduit defined by the outer surface of the catheter and inner surface of the sheath. That is, when the sufficient pressure is achieved in the sheath by the flow of fluid, the flexible tip 406 will expand and allow the fluid to exit from flexible tip 406. The material of the tip may be selected such that from 2 to 30 psi, 5 to 20 psi, or 8 to 12 psi of pressure by the fluid will expand the tip. In one example aspect, the material may be selected such that 10 psi of fluid pressure will expand the tip. Furthermore, the material of the flexible tip 406 may be sufficiently soft to slide along the catheter 102 while maintaining compressive contact with the catheter 102. The material of the tip may be selected such that the force needed to move the tip along the catheter (i.e., a force applied in direction 142 in FIGS. 2-4 and direction 145 in FIGS. 13-15) to is at least 1 gram-force (gf) to at least 6 gf, at least 2 gf to at least 5 gf, or at least 3 gf to at least 4 gf. In one example as aspect, the material may be selected such that the force is at least 3 gf.

Figure 26:
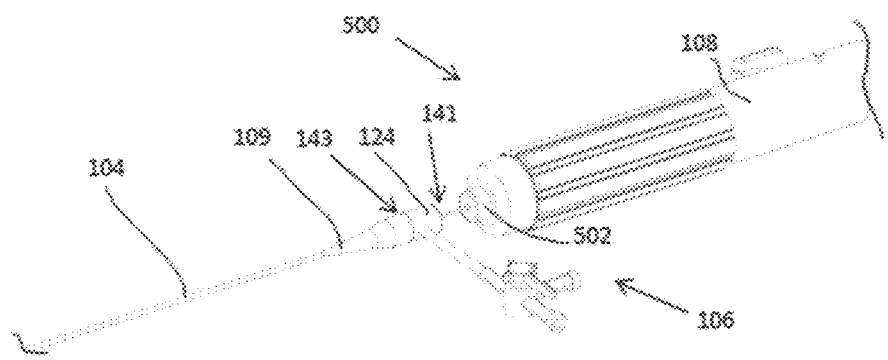
FIG. 26 is a perspective view of another embodiment of an imaging catheter apparatus illustrating a connection feature between the imaging catheter apparatus and a handle.

FIG. 26 is a perspective view of another embodiment of an imaging catheter apparatus illustrating a connection feature between the imaging catheter apparatus and a handle. The imagining catheter apparatus 500 shown in FIG. 26 is similar to the imaging catheter apparatus discussed above, with the difference being that the flow control mechanism 106 is attachable to the handle 108, and the strain relief 109 is attached to the flow control mechanism 106. More specifically the proximal end 141 of the housing member 124 is connectable to the handle 108 and the distal end 143 of the housing member 124 is connected to the strain relief 109. The handle 108 may include a mating portion 502 that corresponds with the proximal end 143 of the housing member 124. The connectability between the flow control mechanism 106 and the handle 108 allows the sheath to be integral with the handle 108 once connected. Thus, the sheath can be easily attached and removed from the handle by the operator, as desired. As noted above, the strain relief 109 is instead located on the distal end 143 of the housing mechanism 124 to allow for the connection with the handle.

While various example embodiments have been described above, it should be understood that all non-mutually exclusive features may be applied to all other example embodiments. In particular, one or more or all of the various features of the sheaths 104, 204, 304, and 404 may be combined in any combination in a single sheath. That is, a single sheath could have, for example, both the holes 206 and the flexible tip 406. Similarly, the connection mechanism discussed above with respect to FIG. 26 may be used in combination any sheath having one or more or all of the features discussed in the various embodiments.

Additionally, in another example embodiment, the imaging catheter assembly may be modified such that the sheath is adjacent to the catheter instead of concentrically surrounding the catheter. That is, instead of the sheath being movable around the catheter, the sheath may be movable alongside the catheter. In such an embodiment the sheath would be in communication with the fluid source via a direct connection with the fluid source instead of via the housing member. That is, the sheath would not pass through the housing member and instead the fluid source may directly provide fluid into the sheath. The sheath may be positioned in the same manner that the catheter is positioned, and then fluid may be directly provided through the proximal end of the sheath to exit the distal end of the sheath. The positioning of the catheter is discussed in more detail below.

Figure 27:
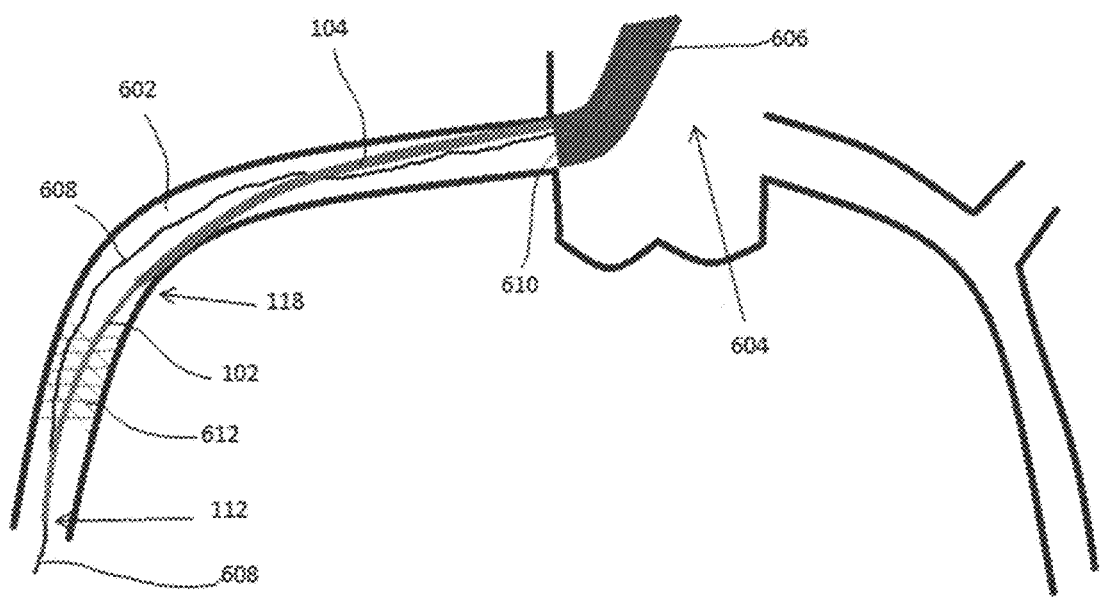
FIG. 27 is a schematic view the example imaging catheter assembly of FIG. 1 positioned inside an artery.

A method of flushing an area within a coronary artery will now be described, with reference to FIG. 27. FIG. 27 is a schematic view showing the imaging catheter assembly 100 inserted into the coronary artery 602 of a patient's aorta 604. The manner in which the catheter 102 may be positioned within the coronary artery 602 may be performed using a guide catheter 606 and a guidewire 608, according to methods known in the art. For example, the guide catheter 606 may first be introduced into the femoral artery. The guide catheter 606 may then be advanced to the ostium 610 of the coronary artery 602. Next, the guidewire 608 may be advanced through the guide catheter 606 and into the coronary artery 602. The guidewire 608 may be continued to be advanced beyond the blockage in the artery. The catheter 102 may then be advanced through the guide catheter 606 and into the coronary artery 602 by "riding" the guidewire 608. That is, the catheter 102 may include a pocket or sheath (not shown) near the distal end 112 that the guidewire 608 may pass through (see for example U.S. Pat. No. 7,241,286, which provides an example of a catheter traveling over a guidewire). Thus, the catheter 102 may be advanced within the coronary artery 602 by traveling along the already-positioned guidewire 608.

Once the catheter 102 has been positioned within the coronary artery 602, the operator may then advance the sheath 104 such that the distal end 118 of the sheath 104 is at the desired position relative to the distal end 112 of the catheter 102. The operator may advance or retract the sheath 104 by moving the entire flow control mechanism 106 forward or backward. Because the proximal end 116 of the sheath 104 is fixed to the housing member 124 of the flow control mechanism 106, the movement of the flow control mechanism 106 in turn moves the sheath 104. In this manner, the operator can move the sheath 104 such that the outlet at the distal end 118 of the sheath 104 is located at a desired position relative to the distal end 112 of the catheter 102. In the example shown in FIG. 27, the distal end 118 of the sheath 104 is located upstream of a stent 612, while the distal end 112 of the catheter 102 is located downstream of the stent 612.

With the catheter 102 and the sheath 104 in the desired positions, the operator may then inject fluid through the sheath 102 via the flow control mechanism 106. The fluid source 133 may be any suitable device for delivering fluid at the necessary pressure to travel through sheath 104, such as a manual or automatic syringe, a fluid container with a pump, and the like. The fluid can also be controlled by actuating the actuator 132 to open communication between the fluid source and the conduit. The fluid will travel through the housing member 124 of the flow control mechanism 106 and into the conduit 150. The fluid will continue to flow through the conduit 150 until it exits out of the distal end 118 of the sheath 104. The rate of flow rate may be from 3 cc/second to 5 cc/second. In one example aspect the flow rate may be 4 cc/second. After exiting the distal end 118 of the sheath 104, the fluid will flush the area around the catheter 102 in a direction toward the distal end 112 of the catheter. The flushing should be sufficient to displace a volume of blood around the area to be imaged via the imaging element 144 near the distal end 112 of the catheter 102. For example, to survey a typical portion of artery wall around the imaging element 144, a cylindrical volume of 50-80 mm or more may be displaced with the flush fluid.

In some embodiments, the automatic syringe injection is controlled by the physician or other user initiating the imaging core pullback sequence through the user interface. The physician or other user may initiate the imaging core pullback sequence and then either the same user or another physician or technician initiates the injection sequence. In other embodiments, the two events are automatically linked so only a single initiation step is required. Embodiments having an automatic injection can be particularly advantageous since the imaging core pullback sequence and the injection sequence can be simultaneously automated through a single user interface (e.g., a patient interface unit).

The flush solution may be, for example, sterile physiological saline, pure contrast solution, or a mixture of sterile saline and angiographic contrast solution. Other fluids may also be appropriate based on the particular application.

Immediately after flushing the desired area with flush solution to displace the blood, the imaging element 144 may be prompted to take an image of the desired area. The prompting of the taking of the image may be done manually or by a computer system as known in the art for OCT systems. That is, the imaging element 144 may be in communication with a computer controlled system such the computer system can both trigger the timing of the image and receive the image. Such example computer systems are described in, but not limited to, U.S. Pat. Nos. 7,872,759; 8,289,522; 8,676,013; 8,928,889; 9,332,942, 9,557,154 and U.S. Patent Publication Nos. 2010/0092389; 2011/0292400; 2012/0101374; 2016/0228097; 2018/0003481; 2017/0135584; 2017/0360398; 2018/0045501 and WO 2016/015052; and WO 2016/144878 each of which patents and patent publications are incorporated by reference herein in their entireties.

While the above method has been described with respect to the sheath 104 shown in FIGS. 1-22, it should be understood that the method can be performed with a sheath having one or more or all of the features shown in FIGS. 23-26.

The above-described apparatus and method thus provides the operator with the ability to control the precise location of the delivery of fluid within the artery relative to the distal end of the catheter.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An imaging catheter assembly comprising:
   a catheter comprising:
      a proximal end;
      a distal end;
      a tubular body extending from the proximal end to the distal end; and
      an imaging element within the tubular body;
   a sheath comprising:
      a proximal end;
      a distal end; and
      a tubular body extending from the proximal end to the distal end, the tubular body having an inner surface,
   wherein the inner surface of the tubular body of the sheath at least partially defines a conduit for conveying a fluid to the distal end of the sheath,
   wherein the sheath is movable either distally or proximally over the catheter to deliver fluid through a tip of the distal end of the sheath only, and
   wherein the delivery of fluid is parallel to a length of the sheath, to a desired target.

2. The imaging catheter assembly of claim 1,
   wherein the sheath coaxially surrounds an outer surface of the catheter, and
   wherein the conduit is defined by the outer surface of the catheter and the inner surface of the sheath.

3. The imaging catheter assembly of claim 1, further comprising a flow control mechanism coupled with the sheath.

4. The imaging catheter assembly of claim 3,
   wherein the flow control mechanism comprises a housing member, and
   wherein the proximal end of the sheath is fixed to the housing member.

5. The imaging catheter assembly of claim 4,
   wherein the housing member comprises a proximal end and a distal end,
   wherein the flow control mechanism comprises a seal member disposed at the proximal end of the housing member, and
   wherein the proximal end of the sheath is fixed to the distal end of the housing member.

6. The imaging catheter assembly of claim 4,
   wherein the housing member surrounds the catheter from the distal end of the housing member to the proximal end of the housing member.

7. The imaging catheter assembly of claim 4, wherein the housing member defines a chamber that is in communication with a fluid source.

8. The imaging catheter assembly of claim 7, wherein the proximal end of the sheath is in communication with the chamber.

9. The imaging catheter assembly of claim 7, wherein the distal end of the sheath is in communication with the chamber.

10. The imaging catheter assembly of claim 4, further comprising a handle coupled with the catheter, wherein the housing member is connectable with the handle.

11. The imaging catheter assembly of claim 3, wherein the flow control mechanism is moveable along the catheter.

12. The imaging catheter assembly of claim 3, wherein moving the flow control mechanism in a direction toward the distal end of the catheter moves the sheath toward the distal end of the catheter.

13. The imaging catheter assembly of claim 1, further comprising:
   a handle coupled with the proximal end of the catheter; and
   a strain relief extending from the handle and surrounding a portion of the catheter.

14. The imaging catheter assembly of claim 1, wherein the imaging element is disposed at the distal end of the catheter.

15. The imaging catheter assembly of claim 1, wherein the sheath comprises one or more holes in proximity to the distal end of the sheath.

16. The imaging catheter assembly of claim 1, wherein the sheath comprises a channel formed on an outer surface of the sheath or on the inner surface of the sheath.

17. The imaging catheter assembly of claim 1, wherein the channel extends from the proximal end of the sheath to the distal end of the sheath.

18. The imaging catheter assembly of claim 1,
   wherein the sheath comprises a flexible tip at the distal end of the sheath.

19. The imaging catheter assembly of claim 18, wherein the flexible tip is biased toward an outer surface of the catheter, and wherein the flexible tip extends away from the outer surface of the catheter under a force sufficient to overcome the bias.

20. An imaging catheter assembly comprising:
a catheter comprising:
  a proximal end;
  a distal end;
  a tubular body extending from the proximal end to the distal end, the tubular body having an outer surface; and
  an imaging element within the tubular body;
a sheath comprising:
  a proximal end;
  a distal end; and
  a tubular body extending from the proximal end to the distal end, the tubular body having an inner surface,
wherein the tubular body of the sheath coaxially surrounds the tubular body of the catheter to form an annular conduit defined by the outer surface of the tubular body of the catheter and the inner surface of the tubular body of the sheath, the annular conduit providing a pathway for conveying fluid to the distal end of the sheath,
wherein the sheath is movable along the outer surface of the tubular body of the catheter either distally or proximally to deliver fluid through a tip of the distal end of the sheath only and parallel to a length of the sheath, to a desired target.

21. A method of flushing an area within a coronary artery comprising:
providing an imaging catheter assembly comprising:
  a catheter comprising:
    a proximal end;
    a distal end;
    a tubular body extending from the proximal end to the distal end; and
    an imaging element within the tubular body;
  a sheath comprising:
    a proximal end;
    a distal end; and
    a tubular body extending from the proximal end to the distal end, the tubular body having an inner surface,
  wherein the inner surface of the tubular body of the sheath at least partially defines a conduit;
inserting the distal end of the catheter into the coronary artery to a predetermined position relative to the area within the coronary artery;
positioning the distal end of the sheath to a predetermined position relative to the catheter by advancing or retracting the sheath over the catheter to deliver fluid through a tip of the distal end of the sheath and parallel to a length of the sheath, to the predetermined position near the distal end of the sheath; and
conveying a fluid out of the distal end of the sheath only via the conduit to flush the area within the coronary artery.

* * * * *